United States Patent
Fingler et al.

(10) Patent No.: US 9,763,570 B2
(45) Date of Patent: Sep. 19, 2017

(54) OPTICAL COHERENCE TOMOGRAPHY (OCT) SYSTEM WITH PHASE-SENSITIVE B-SCAN REGISTRATION

(71) Applicants: UNIVERSITY OF SOUTHERN CALIFORNIA, Los Angeles, CA (US); CALIFORNIA INSTITUTE OF TECHNOLOGY, Pasadena, CA (US)

(72) Inventors: Jeffrey P. Fingler, Orange, CA (US); Scott E. Fraser, Glendale, CA (US)

(73) Assignees: UNIVERSITY OF SOUTHERN CALIFORNIA, Los Angeles, CA (US); CALIFRONIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/106,910

(22) PCT Filed: Feb. 4, 2015

(86) PCT No.: PCT/US2015/014468
§ 371 (c)(1),
(2) Date: Jun. 21, 2016

(87) PCT Pub. No.: WO2015/120055
PCT Pub. Date: Aug. 13, 2015

(65) Prior Publication Data
US 2017/0020387 A1    Jan. 26, 2017

Related U.S. Application Data

(60) Provisional application No. 61/935,431, filed on Feb. 4, 2014.

(30) Foreign Application Priority Data

Feb. 4, 2015 (WO) .................... PCT/US15/14410

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *A61B 3/10* (2013.01); *A61B 3/1233* (2013.01);
(Continued)

(58) Field of Classification Search
CPC ......... A61B 3/102; A61B 3/10; A61B 3/0025; A61B 3/1233; G01L 39/02091; G02B 6/0005
(Continued)

(56) References Cited

U.S. PATENT DOCUMENTS

2008/0025570 A1*  1/2008  Fingler .................. A61B 3/102
                                                               382/107
2009/0005691 A1    1/2009  Huang et al.
(Continued)

OTHER PUBLICATIONS

Fingler, J. et al. 2007. Mobility and Transverse Flow Visualization Using Phase Variance Contrast with Spectral Domain Optical Coherence Tomography. Optics Express, vol. 15, No. 20, Sep. 18, 2007, pp. 12636-12653.
(Continued)

*Primary Examiner* — William R Alexander
(74) *Attorney, Agent, or Firm* — McDermott Will & Emery LLP

(57) ABSTRACT

This disclosure relates to the field of Optical Coherence Tomography (OCT). This disclosure particularly relates to an OCT system having a configuration that uses a phase sensitive B-scan registration method. In this disclosure, an OCT system may have a configuration that scans a physical object, acquires OCT signals to form B-scans, uses these
(Continued)

B-scans to determine an optimal shift in an axial direction by using total phase error between B-scans, and align B-scans, thereby minimizing effects of motion that may occur during scanning of the physical object.

14 Claims, 11 Drawing Sheets

(51) Int. Cl.
  *A61B 3/12* (2006.01)
  *G01B 9/02* (2006.01)
  *F21V 8/00* (2006.01)
  *G01N 21/47* (2006.01)

(52) U.S. Cl.
  CPC ....... *G01B 9/02091* (2013.01); *G02B 6/0005* (2013.01); *G01N 21/4795* (2013.01)

(58) Field of Classification Search
  USPC .................................................. 351/206, 205
  See application file for complete search history.

(56) References Cited

U.S. PATENT DOCUMENTS

| | | | |
|---|---|---|---|
| 2009/0015842 A1* | 1/2009 | Leitgeb | A61B 5/7257 356/456 |
| 2011/0102802 A1* | 5/2011 | Izatt | A61B 3/102 356/479 |
| 2011/0170111 A1* | 7/2011 | Rolland | G01B 9/021 356/479 |
| 2013/0100458 A1 | 4/2013 | Yamada | |
| 2013/0289882 A1 | 10/2013 | Sharma et al. | |
| 2014/0028997 A1* | 1/2014 | Cable | G01B 9/02091 356/51 |
| 2014/0104618 A1* | 4/2014 | Potsaid | G02B 26/105 356/497 |
| 2014/0218684 A1* | 8/2014 | Kumar | A61B 3/14 351/206 |

OTHER PUBLICATIONS

Hillmann, D. et al. 2012. Common Approach for Compensation of Axial Motion Artifacts in Swept-Source OCT and Dispersion in Fourier-Domain OCT. Optics Express, vol. 20, No. 6, Mar. 12, 2012, pp. 6761-6776.

USPTO. 2015. International Search Report and Written Opinion of the US International Searching Authority (ISA/US), dated May 14, 2015, for PCT Application PCT/US2015/014468, entitled "Optical Coherence Tomography (OCT) System with Phase-Sensitive B-Scan Registration," of which instant application is a 371 national phase filing.

\* cited by examiner

OPTICAL COHERENCE TOMOGRAPHY (OCT) SYSTEM WITH PHASE-SENSITIVE B-SCAN REGISTRATION

CROSS-REFERENCE TO RELATED APPLICATIONS

This application is a national phase application under 35 U.S.C. 371 of International Application No. PCT/US2015/014468, filed on Feb. 4, 2015, entitled "Optical Coherence Tomography (OCT) System with Phase-Sensitive B-Scan Registration,"; which is based upon and claims priority to U.S. provisional patent application 61/935,431, entitled "OCT Phase-Sensitive B-scan Registration Algorithm," filed Feb. 4, 2014. This application is also based upon and claims priority to Patent Cooperation Treaty (PCT) application No. PCT/US15/14410, entitled "Optical Coherence Tomography (OCT) with Improved Motion Contrast," filed Feb. 4, 2015. The entire contents of this provisional patent application and PCT application are incorporated herein by reference.

STATEMENT REGARDING FEDERALLY SPONSORED RESEARCH

This invention was made with government support under Grant No. NIH STTR 1 R41 EY021054 awarded by National Institutes of Health (NIH). The government has certain rights in the invention.

BACKGROUND

Technical Field

This disclosure relates to the field of Optical Coherence Tomography (OCT). This disclosure particularly relates to an OCT system with phase sensitive B-scan registration. This disclosure also particularly relates to methods for phase-sensitive B-scan registration for the OCT system.

Description of Related Art

Optical coherence tomography (OCT) has become an indispensable clinical imaging tool, since its introduction in 1991. For a background of OCT technology, see, for example, Drexler and Fujimoto et al. "Optical Coherence Technology: Technology and Applications" Springer, Heidelberg, Germany, 2008. This book is incorporated herein by reference in its entirety. OCT is based on an optical measurement technique known as low-coherence interferometry. OCT performs high resolution, cross-sectional imaging of internal microstructure of a physical object by directing a light beam to the physical object, and then measuring and analyzing magnitude and time delay of backscattered light.

A cross-sectional image is generated by performing multiple axial measurements of time delay (axial scans or A-scans) and scanning the incident optical beam transversely. This produces a two-dimensional data set of A-scans (i.e. B-scans), which represents the optical backscattering in a cross-sectional plane through the physical object. Three-dimensional, volumetric data sets can be generated by acquiring sequential cross-sectional images by scanning the incident optical beam in a raster pattern (three-dimensional OCT or 3D-OCT). This technique yields internal microstructural images of the physical objects with very fine details. For example, pathology of a tissue can effectively be imaged in situ and in real time with resolutions smaller than 15 micrometers.

Several types of OCT systems and methods have been developed, for example, Time-domain OCT (TD-OCT) and Fourier-domain OCT (FD-OCT). Use of FD-OCT enables high-resolution imaging of retinal morphology that is nearly comparable to histologic analysis. Examples of FD-OCT technologies include Spectral-domain OCT (SD-OCT) and Swept-source OCT (SS-OCT).

OCT may be used for identification of common retinovascular diseases, such as age-related macular degeneration (AMD), diabetic retinopathy (DR), and retinovascular occlusions. However, despite the rapid evolution of OCT imaging, current OCT technology may not provide adequate visualization of retinal and choroidal microvasculature. Thus, clinicians are often compelled to order both OCT and fluorescein angiography (FA) in patients with the retinovascular diseases. There has been increased interest in using data generated during FD-OCT imaging to generate angiographic images of the fundus. These angiograms are implemented non invasively without injection of fluorescent dye.

Recently, phase-variance OCT (PV-OCT) has been introduced to image retinal microvasculature. See, for example, Fingler et al. "Dynamic Motion Contrast and Transverse Flow Estimation Using Optical Coherence Tomography" U.S. Pat. No. 7,995,814; Fingler et al. "Dynamic Motion Contrast and Transverse Flow Estimation Using Optical Coherence Tomography" U.S. Pat. No. 8,369,594; Fingler et al. "Mobility and transverse flow visualization using phase variance contrast with spectral domain optical coherence tomography" Opt. Express 2007; 15:12636-53; Fingler et al. "Phase-contrast OCT imaging of transverse flows in the mouse retina and choroid. Invest Ophthalmol. Vis. Sci. 2008; 49:5055-9; Fingler et al. "Volumetric microvascular imaging of human retina using optical coherence tomography with a novel motion contrast technique" Opt. Express [serial online] 2009; 17:22190-200; Kim et al. "In vivo volumetric imaging of human retinal circulation with phase-variance optical coherence tomography" Biomed Opt Express [serial online] 2011; 2:1504-13; Kim et al. "Non-invasive imaging of the foveal avascular zone with high-speed, phase-variance optical coherence tomography" Invest. Ophthalmol. Vis. Sci. 2012; 53:85-92; and Kim et al. "Optical imaging of the chorioretinal vasculature in the living human eye" PNAS, Aug. 27, 2013, vol. 110, no. 35, 14354-14359. All these publications and patent disclosures are incorporated herein by reference in their entirety.

PV-OCT uses software processing of data normally acquired, but not used, during FD-OCT imaging. With a different scanning protocol than found in commercial instruments, PV-OCT identifies regions of motion between consecutive B-scans that are contrasted with less mobile regions. In the retina and choroid, the regions with motion correspond to the vasculature; these vessels are readily differentiated from other retinal tissues that are relatively static.

An alternative method to acquire images of the retinal vasculature is Doppler OCT, which measures the change in scatterer position between successive depth scans and uses this information to calculate the flow component parallel to the imaging direction (called axial flow). Doppler OCT has been used to image large axial flow in the retina, but without dedicated scanning protocols this technique is limited in cases of slow flow or flow oriented transverse to the imaging direction. Because this technique depends on measuring motion changes between successive depth scans, as imaging speed improvements continue for FD-OCT systems, the scatterers have less time to move between measurements and the slowest motions become obscured by noise. This further reduces the visualization capabilities of typical Doppler OCT techniques.

In contrast, PV-OCT will be able to achieve the same time separations between phase measurements with increased FD-OCT imaging speeds, maintaining the demonstrated ability to visualize fast blood vessel and slow microvascular flow independently of vessel orientation.

Several groups in recent years have developed OCT imaging methods to push beyond conventional Doppler OCT imaging limitations. Some approaches involve increasing the flow contrast through hardware modifications of FD-OCT machines, such as in 2-beam scanning, or producing a heterodyne frequency for extracting flow components. Other investigators have used nonconventional scanning patterns or repeated B-scan acquisitions, such as used in PV-OCT to increase the time separation between phase measurements and enhance Doppler flow contrast of microvascular flow. In addition to phase-based contrast techniques to visualize vasculature, intensity-based visualization of microvasculature has been developed for OCT using segmentation, speckle-based temporal changes, decorrelation-based techniques, and contrast based on both phase and intensity changes. Each of these methods has varying capabilities in regard to microvascular visualization, noise levels, and artifacts while imaging retinal tissues undergoing typical motion during acquisition. Some of the noise and artifact limitations can be overcome with selective segmentation of the volumetric data or increased statistics through longer imaging times, but further analysis is required to be able to compare all of the visualization capabilities from all these different systems.

For further description of OCT methods and systems, and their applications, for example, see: Schwartz et al. "Phase-Variance Optical Coherence Tomography: A Technique for Noninvasive Angiography" American Academy of Ophthalmology, Volume 121, Issue 1, January 2014, Pages 180-187; Sharma et al. "Data Acquisition Methods for Reduced Motion Artifacts and Applications in OCT Angiography" U.S. Pat. No. 8,857,988; Narasimha-Iyer et al. "Systems and Methods for Improved Acquisition of Ophthalmic Optical Coherence Tomography Data" U.S. Patent Application Publication No. 2014/0268046; Everett "Methods for Mapping Tissue With Optical Coherence Tomography Data" U.S. Pat. No. 7,768,652. All these publications and patent disclosures are incorporated herein by reference in their entirety.

SUMMARY

This disclosure relates to the field of Optical Coherence Tomography (OCT). This disclosure particularly relates to an OCT system with phase sensitive B-scan registration. This disclosure particularly relates to methods for phase-sensitive B-scan registration for the OCT system.

For example, the OCT system may have a configuration that scans a physical object that has a surface and a depth with a beam of light that has a beam width and a direction; acquires OCT signals from the scan; generates discretized A-scan data and B-scan data from the acquired OCT signals; assigns the discretized A-scan data into pixels; forms at least one B-scan cluster set using the acquired OCT signals that includes at least one B-scan cluster that includes at least two B-scans that are parallel to one another and form planes that are parallel to the direction of the beam of light; and forms B-scan pairs from the at least two B-scans.

The OCT system may further have a configuration that (a) calculates a total phase error for each B-scan pair and shifts one B-scan of each B-scan pair in a direction parallel to the direction of the beam of light at least two times, or (b) shifts one B-scan of each B-scan pair in a direction parallel to the direction of the beam of light at least three times; wherein each shift is one pixel and parallel to the beam of light.

The OCT system may further have a configuration that calculates a total phase error for each B-scan pair after each shift; identifies the smallest calculated total phase error among all of the calculated total phase errors for each B-scan pair; identifies the shift amount for each B-scan pair that resulted in the identified smallest calculated total phase error; calculates a cumulative axial shift for each B-scan within the at least one B-scan cluster; and aligns all B-scans within the at least one B-scan cluster.

The OCT system may also have a configuration that, after forming B-scan pairs, calculates phase differences for each B-scan pair; and wherein each total phase error may be calculated using the calculated phase differences, wherein each calculated phase difference may constitute a phase difference data point. The phase difference data points may be used to calculate a bulk motion phase difference.

The calculated bulk motion phase difference may be corrected for effects of bulk motion to provide a corrected phase difference.

A thresholding method based on intensity may be applied to the corrected phase difference to decrease effects of noise.

The OCT system may have a configuration that uses the aligned B-scans to form an image of the physical object. The physical object may be human tissue.

The OCT system may comprise at least one light source that provides at least one light beam; at least one retro-reflector; at least one optical fiber coupler or at least one free space coupler that guides the at least one light beam to the physical object and to at least one retro-reflector. The at least one light beam guided to the physical object may forms at least one backscattered light beam. The at least one light beam guided to the at least one retro-reflector may form at least one reflected reference light beam.

The OCT system may further comprise at least one scanning optic that scans the at least one light beam over the physical object; at least one detector. The detector may combine the at least one backscattered light beam and the at least one reflected light beam to form light interference, detect magnitude and time delay of the at least one backscattered light beam, and form OCT signals. The at least one optical fiber coupler or the at least one free space coupler may guide the at least one backscattered light beam and the at least one reflected light beam to the at least one detector.

The OCT system may further comprise at least one processor that obtains and analyzes the OCT signals formed by the at least one detector, and forms at least one image of the physical object; and at least one display that displays the at least one image of the physical subject.

The OCT system may have a configuration that identifies regions of motion based on intensity or phase variations between B-scans. The OCT system may have a configuration that identifies the regions of motion, for example, by using a Phase Variance OCT (PV-OCT) method, a Phase Contrast OCT (PC-OCT) method, an Intensity/Speckle Variance OCT (IV-OCT) method, a Doppler OCT (D-OCT) method, a Power of Doppler Shift OCT (PDS-OCT) method, a Split Spectrum Amplitude Decorrelation Analysis (SSADA) method, an Optical Micro-angiography (OMAG) method, a Correlation Mapping OCT (cmOCT) method, or a combination thereof. The OCT system may have a configuration that may use a Phase Variance OCT (PV-OCT) method.

A non-transitory, tangible, computer-readable storage media containing a program of instructions that may cause a computer system running the program of instructions to function as an optical coherence tomography (OCT) system ("storage media") is also within the scope of this disclosure.

The storage media may have a configuration that scans a physical object that has a surface and a depth with a beam of light that has a beam width and a direction; acquires OCT signals from the scan; generates discretized A-scan data and B-scan data from the acquired OCT signal; assigns the discretized A-scan data into pixels; forms at least one B-scan cluster set using the acquired OCT signals that each includes at least one B-scan cluster that includes at least two B-scans that are parallel to one another and forms planes that are parallel to the direction of the beam of light; and forms B-scan pairs from the at least two B-scans in each B-scan cluster. The storage media may also have a configuration that does either of the following: (a) calculate a total phase error for each B-scan pair before any shift of any B-scan and then shifts one B-scan of each B-scan pair at least two times, or (b) shifts one B-scan of each B-scan pair at least three times. Each shift may be one pixel and in a direction parallel to the beam of light. The storage media may also have a configuration that calculates a total phase error for each B-scan pair after each shift; identifies the smallest calculated total phase error among all of the calculated total phase errors for each B-scan pair; identifies the shift amount for each B-scan pair that resulted in the identified smallest calculated total phase error; calculates a cumulative axial shift for each B-scan within the at least one B-scan cluster; and aligns all B-scans within the at least one B-scan cluster.

The program of instructions may cause the computer system running the program of instructions to: obtain and analyze the OCT signals formed by at least one detector, and form at least one image of the physical object; and display the at least one image of the physical subject.

Any combination of above systems, storage media and methods are within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Figure 1:
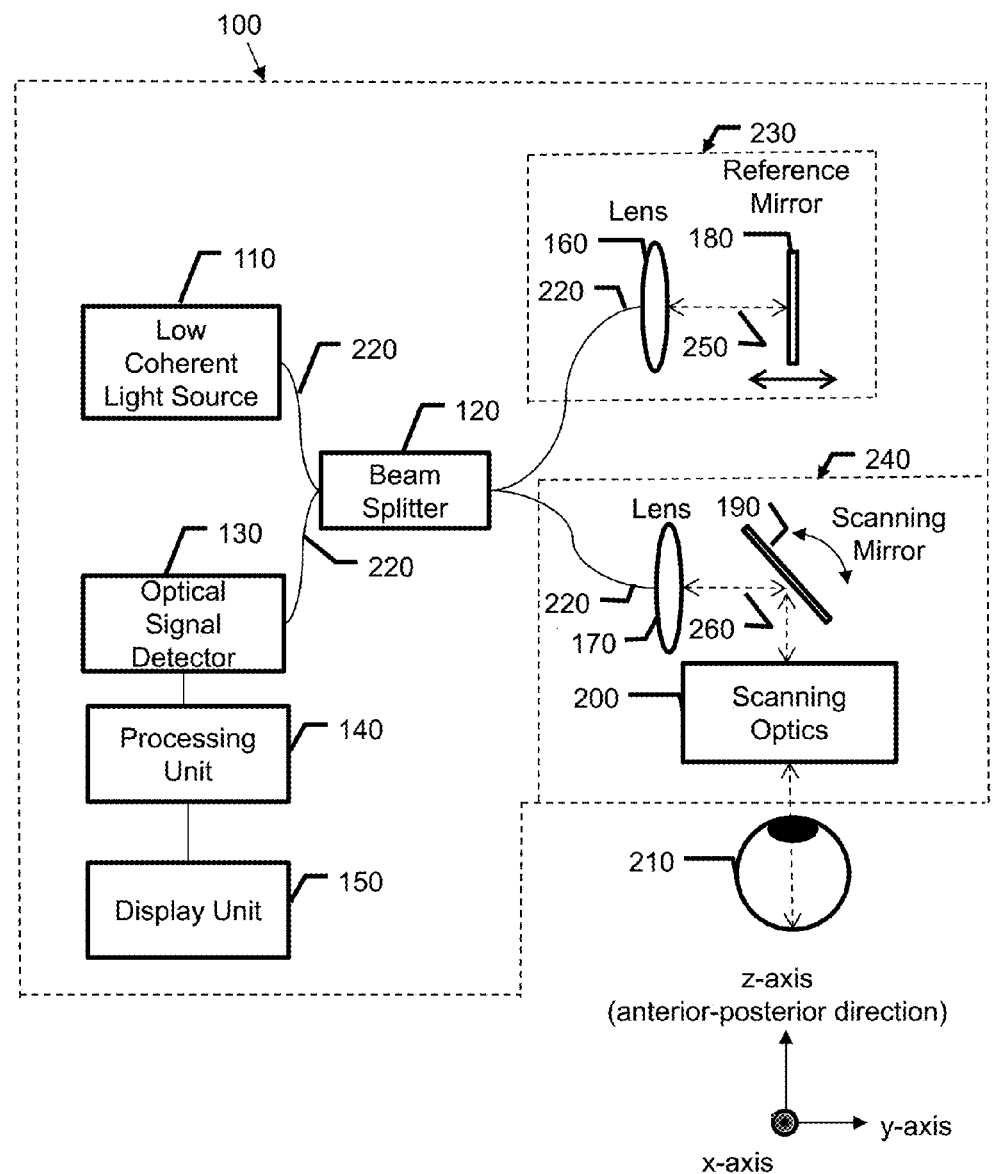
FIG. 1 is schematics of a generalized OCT system.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

This disclosure relates to the field of Optical Coherence Tomography (OCT). This disclosure particularly relates to an OCT system having a configuration that uses a phase sensitive B-scan registration method. This disclosure particularly relates to methods for phase-sensitive B-scan registration for the OCT system.

This disclosure relates to an OCT system. The OCT system may comprise any interferometer that have any optical design comprising, such as Michelson interferometer, Mach-Zehnder interferometer, Gires-Tournois interferometer, common-path based designs, or other interferometer architectures. The sample and reference arms in the interferometer may consist of any type of optics, for example bulk-optics, fiber-optics, hybrid bulk-optic systems or the like.

The OCT system may also comprise any basic OCT system. Examples of the basic OCT system may include Time-domain OCT (TD-OCT) and Fourier-domain, or Frequency-domain, OCT (FD-OCT). Examples of the FD-OCT may include Spectral-domain OCT (SD-OCT), Swept Source OCT (SS-OCT), and Optical frequency domain Imaging (OFDI).

The OCT system may have a configuration that uses any OCT approaches that identifies and/or visualizes regions of motion ("OCT motion contrast approach"). The OCT motion contrast approach may use motion occurring within the physical object to identify and/or visualize regions with improved contrast. For example, variation of OCT signals caused by blood flow in blood vessels may be used by OCT to identify and/or visualize a choroidal vasculature through image contrast important. As a result, better images are obtained and/or structures that cannot be identified through a typical OCT system before becomes visible. For example, choriocapillaris may become visible by using the OCT motion contrast method. Examples of the OCT motion contrast method may include Phase Variance OCT (PV-OCT), Phase Contrast OCT (PC-OCT), Intensity/Speckle Variance OCT (IV-OCT), Doppler OCT (D-OCT), Power of Doppler Shift OCT (PDS-OCT), Split Spectrum Amplitude Decorrelation Analysis (SSADA), Optical Micro-angiography (OMAG), Correlation Mapping OCT (cmOCT), and the like. Examples of the PV-OCT method are disclosed by Fingler et al. "Dynamic Motion Contrast and Transverse Flow Estimation Using Optical Coherence Tomography" U.S. Pat. No. 7,995,814; Fingler et al. "Dynamic Motion Contrast and Transverse Flow Estimation Using Optical Coherence Tomography" U.S. Pat. No. 8,369,594; Fingler et al. "Mobility and transverse flow visualization using phase variance contrast with spectral domain optical coherence tomography" Opt. Express [serial online] 2007; 15:12636-53; examples of the Speckle Variance OCT method are disclosed by Mariampillai et al. "Speckle variance detection of microvasculature using swept-source optical coherence tomography," Opt. Lett. 33(13), 1530-1532 (2008); examples of the Correlation Mapping OCT method are disclosed by Enfield et al. "In vivo imaging of the microcirculation of the volar forearm using correlation mapping optical coherence tomography (cmOCT)" Biomed. Opt. Express 2, 1184-1193 (2011); examples of the OMAG method are disclosed by An et al. "In vivo volumetric imaging of vascular perfusion within human retina and choroids with optical micro-angiography" Opt. Express 16, 11438-11452 (2008); examples of the Power Doppler OCT method are disclosed by Makita et al. "Optical coherence angiography" Opt. Express 14, 7821-7840 (2006); examples of the SSADA method are disclosed by Jia et al. "Split-spectrum amplitude-decorrelation angiography with optical coherence tomography," Opt. Express20(4), 4710-4725 (2012). Entire contents of these disclosures are incorporated herein by reference.

The OCT system 100 may comprise at least one light source 110, at least one scanning optic 200, at least one retro-reflector 180, at least one optical fiber coupler 220 or at least one free space coupler, at least one detector 130, at least one processing unit 140, and at least one display unit 150.

Examples of a generalized OCT system schematically shown in FIG. 1 are disclosed by Fingler et al. "Dynamic Motion Contrast and Transverse Flow Estimation Using Optical Coherence Tomography" U.S. Pat. No. 7,995,814; Fingler et al. "Dynamic Motion Contrast and Transverse Flow Estimation Using Optical Coherence Tomography" U.S. Pat. No. 8,369,594; and Sharma et al. in a U.S. Pat. No. 8,857,988, entitled "Data Acquisition Methods for Reduced Motion Artifacts and Applications in OCT Angiography". These disclosures are incorporated herein by reference in their entirety. The OCT system 100 may comprise this generalized OCT system.

The at least one light source 110 may comprise any light source, for example, a low coherent light source. Light from the light source 110 may be guided, typically by using at least one optical fiber 220 to illuminate a physical object 210. An example of the physical object 210 may be any tissue in a human eye. For example, the tissue may be a retina. The light source 110 may be either a broadband low coherence light source with short temporal coherence length in the case of SD-OCT or a wavelength tunable laser source in the case of SS-OCT. The light may be scanned, typically with a scanning optic 200 between the output of the optical fiber 220 and the physical object 210, so that a beam of light (dashed line) guided for the physical object 210 is scanned laterally (in x-axis and/or y-axis) over the area or volume to be imaged. The scanning optic 200 may comprise any optical element suitable for scanning. The scanning optic 200 may comprise at least one component. The at least one component of the scanning optic 200 may be an optical component. Light scattered from the physical object 210 may be collected, typically into the same optical fiber 220 used to guide the light for the illumination of the physical object 210. (The physical object 210 is shown in FIG. 1 only to schematically demonstrate the physical object 210 in relation to the OCT system 100. The physical object 210 is not a component of the OCT system 100.)

The OCT system 100 may further comprise a beam splitter 120 to split and guide the light provided by the light source 110 to a reference arm 230 and a physical object arm 240. The OCT system may also further comprise a lens 160 placed between the beam splitter 120 and the retro-reflector 180. The OCT system may also further comprise another lens 170 placed between the beam splitter 120 and the scanning optic 200.

Reference light 250 derived from the same light source 110 may travel a separate path, in this case involving the optical fiber 220 and the retro-reflector 180 with an adjustable optical delay. The retro-reflector 180 may comprise at least one component. The at least one component of the retro-reflector 180 may be an optical component, for example, a reference mirror. A transmissive reference path may also be used and the adjustable delay may be placed in the physical object arm 240 or the reference arm 230 of the interferometer 100.

Collected light 260 scattered from the physical object 210 may be combined with reference light 250, typically in the fiber coupler to form light interference in the detector 130, thereby forming an OCT signal. Although a single optical fiber port is shown going to the detector 130, various designs of interferometers may be used for balanced or unbalanced detection of the interference signal for SS-OCT or a spectrometer detector for SD-OCT.

The output from the detector 130 may be supplied to the processor 140. Results may be stored in the processor 140 or displayed on the display 150. The processing and storing functions may be localized within the OCT system or functions may be performed on an external processing unit to which the collected data is transferred. This external unit may be dedicated to data processing or perform other tasks that are quite general and not dedicated to the OCT system.

Light beam as used herein should be interpreted as any carefully directed light path. In time-domain systems, the reference arm 230 may need to have a tunable optical delay to generate interference. Balanced detection systems may typically be used in TD-OCT and SS-OCT systems, while spectrometers may be used at the detection port for SD-OCT systems.

The interference may cause the intensity of the interfered light to vary across the spectrum. The Fourier transform of the interference light may reveal the profile of scattering intensities at different path lengths, and therefore scattering as a function of depth (z-axis direction) in the physical object. See for example Leitgeb et al. "Ultrahigh resolution Fourier domain optical coherence tomography," Optics Express 12(10):2156, 2004. The entire content of this publication is incorporated herein by reference.

Figure 2:
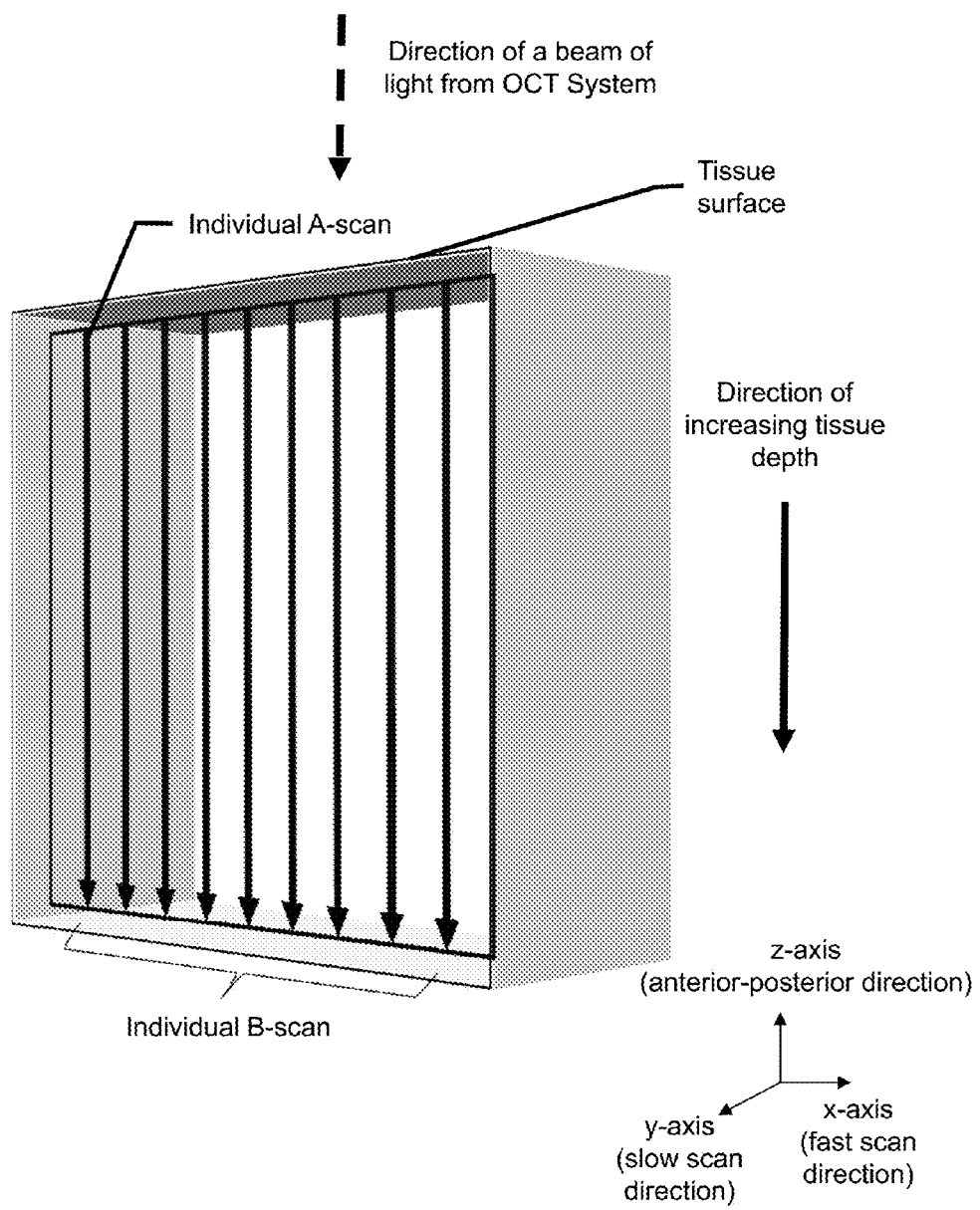
FIG. 2 schematically illustrates a scanning configuration for the OCT system.

The profile of scattering as a function of depth is called an axial scan (A-scan), as schematically shown in FIG. 2. A set of A-scans measured at neighboring locations in the physical object produces a cross-sectional image (tomogram or B-scan) of the physical object. A collection of individual B-scans collected at different transverse locations on the sample makes up a data volume or cube. Three-dimensional C-scans can be formed by combining a plurality of B-scans. For a particular volume of data, the term fast axis refers to the scan direction along a single B-scan whereas slow axis refers to the axis along which multiple B-scans are collected.

B-scans may be formed by any transverse scanning in the plane designated by the x-axis and y-axis. B-scans may be formed, for example, along the horizontal or x-axis direction, along the vertical or y-axis direction, along the diagonal of x-axis and y-axis directions, in a circular or spiral pattern, and combinations thereof. The majority of the examples discussed herein may refer to B-scans in the x-z axis directions but this disclosure may apply equally to any cross sectional image.

Figure 3:
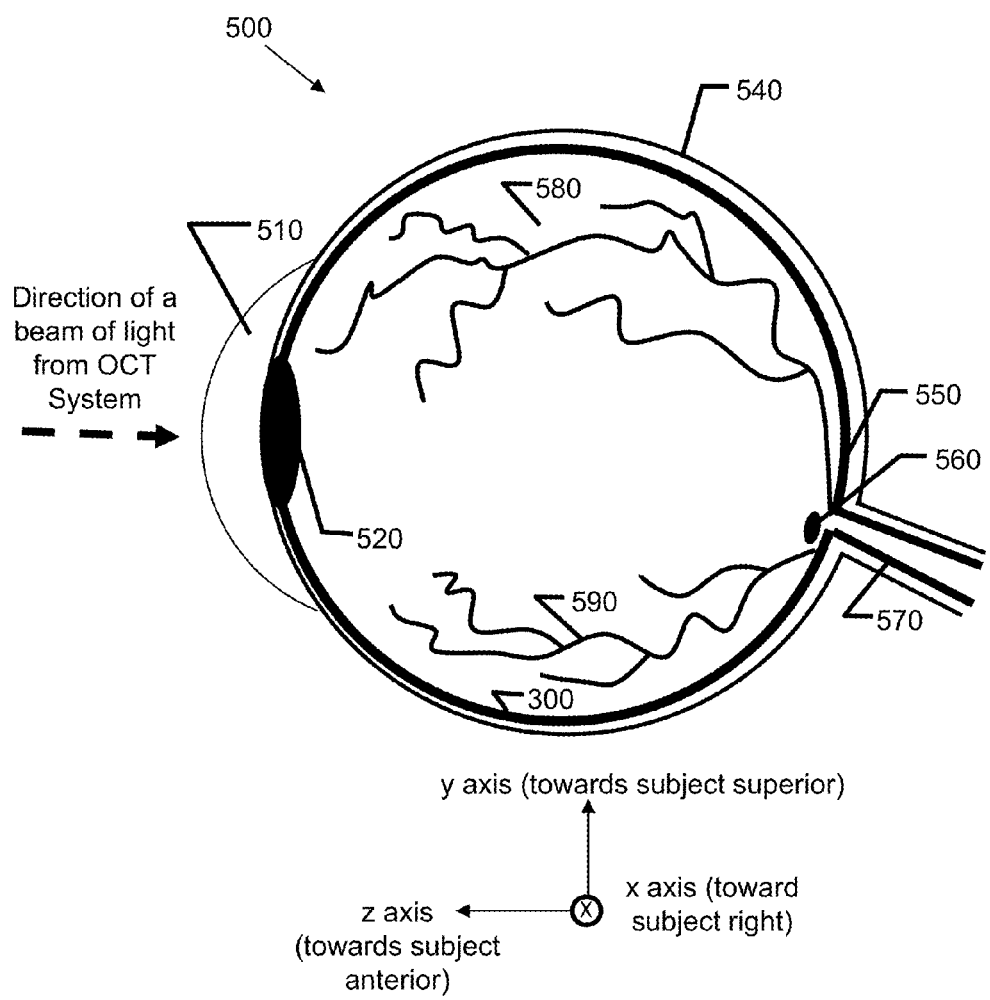
FIG. 3 schematically illustrates sagittal view of a left human eye.

The physical object 210 may be any physical object. The physical object 210 may be a human eye, 500, as shown in a simplified manner in FIG. 3. The human eye comprises a cornea 510, a pupil 520, a retina 300, a choroid 540, a fovea region 550, an optic disk 560, an optic nerve 570, a vitreous chamber 580, and retinal blood vessels 590.

Figure 4:
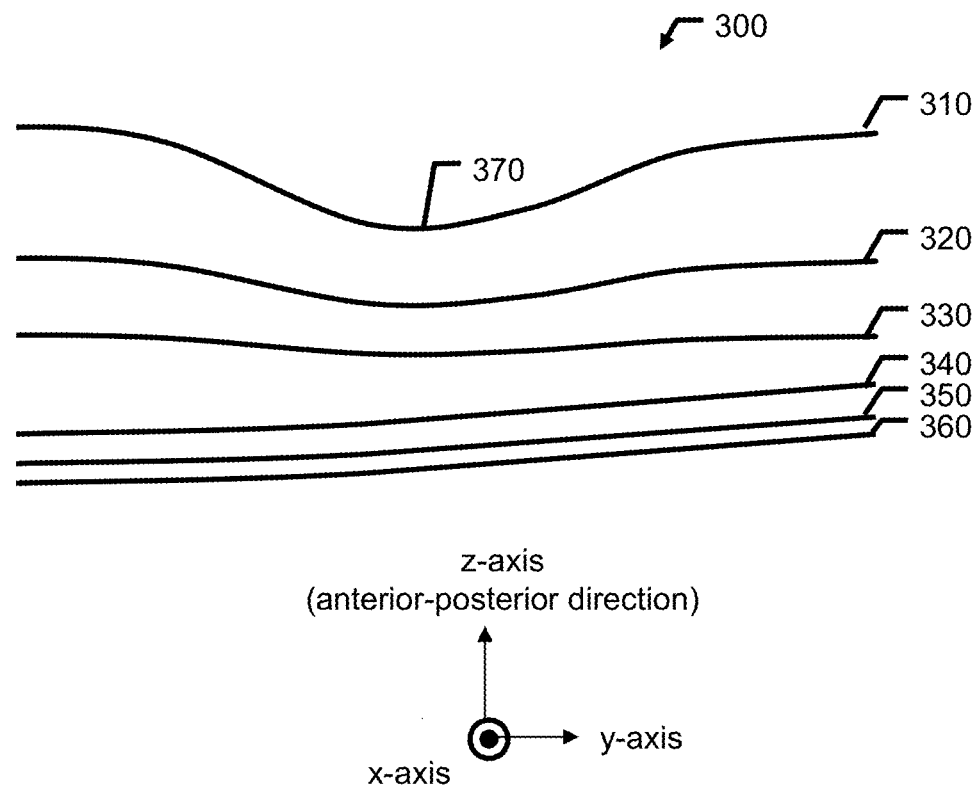
FIG. 4 schematically illustrates cross sectional layers of a retina.
Figure 5:
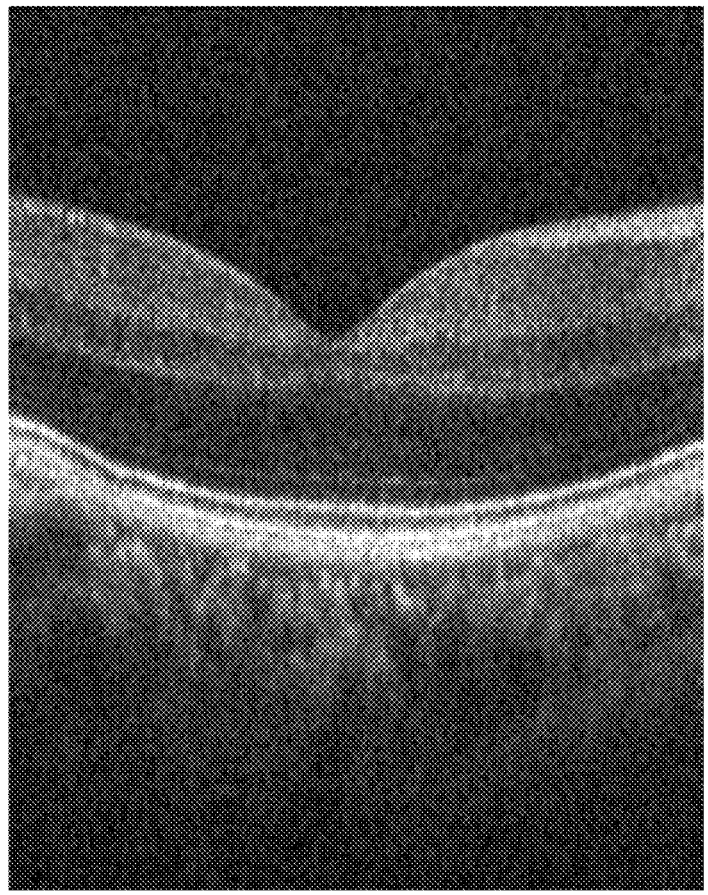
FIG. 5 shows a cross-sectional OCT image of the fovea region of the retina.
Figure 5:
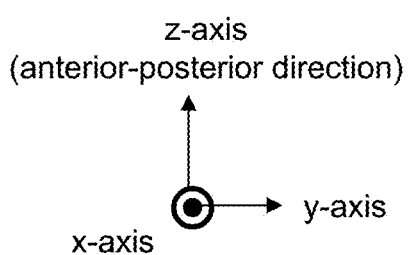

The physical object 210 may be a tissue. An example of the tissue is a retina. A simplified cross-sectional image of layers of the retina 300 is schematically shown in FIG. 4. The retinal layers comprise a Nerve Fiber Layer (NFL) 310, External Limiting Membrane (ELM) 320 Inner/Outer Photoreceptor Segment 330, Outer Photoreceptor Segment 340, Retinal Pigment Epithelium (RPE) 350, Retinal Pigment Epithelium (RPE)/Bruch's Membrane Complex 360. FIG. 4 also schematically shows the fovea 370. FIG. 5 shows a cross-sectional OCT image of the fovea region of the retina.

The OCT system may comprise a method that provides at least one OCT system to acquire data to form at least one A-scan and at least one B-scan by scanning a physical object with at least one beam of light. The at least one OCT system may be any OCT system as disclosed above.

The physical object may comprise any physical object as disclosed above. The physical object has a surface and a depth. For example, a fundus of an eye has an outer surface receiving light from outside environment through pupil. The fundus of an eye also has a depth starting at and extending from its outer surface.

In this disclosure, a z-axis is an axis parallel to the beam of light extending into the depth of the physical object ("axial axis"), the x-axis and the y-axis ("transverse axes") are transverse, thereby perpendicular axes to the z-axis. Orientation of these three axes is shown in FIGS. 1-5 and 7.

Figure 6:
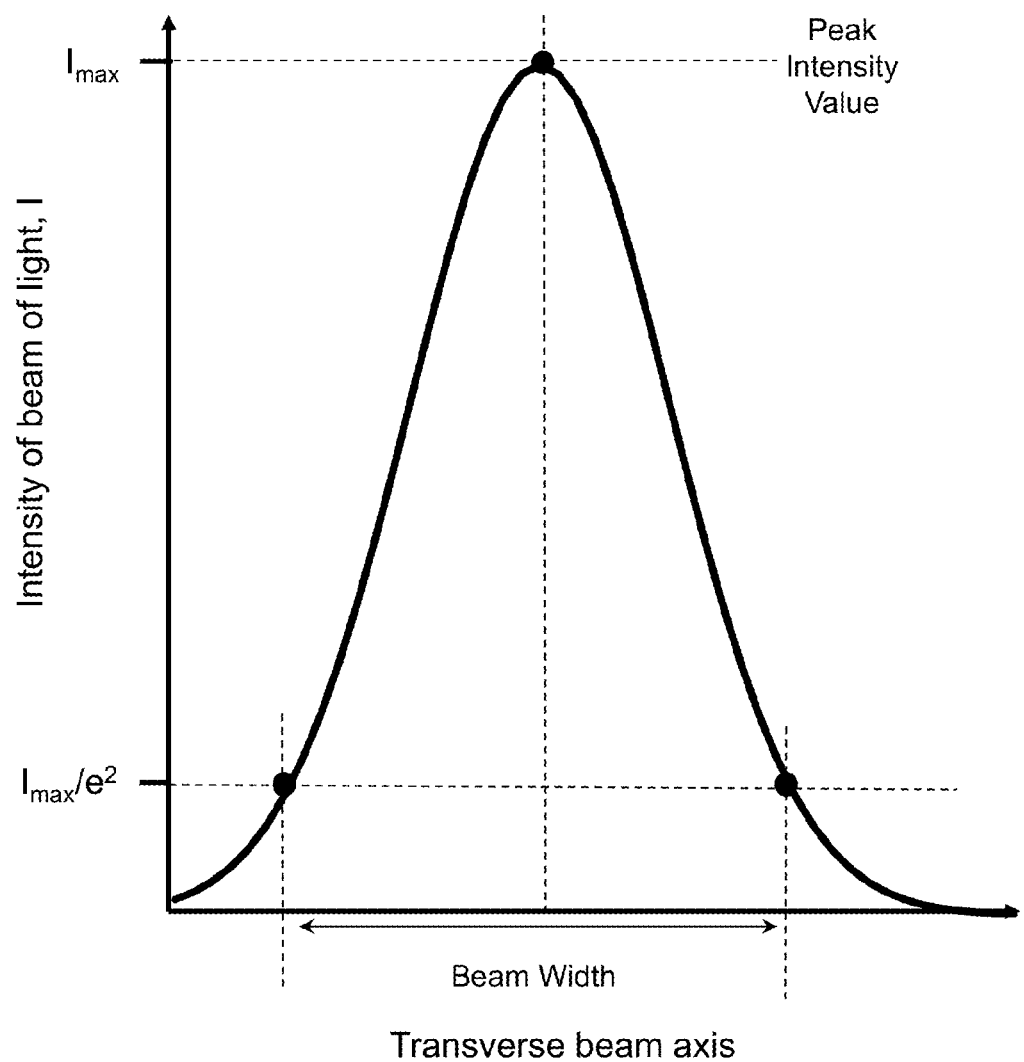
FIG. 6 shows an example of an intensity distribution of a beam of light, transverse to the propagation direction.

The at least one beam of light provided by the OCT system has a width and an intensity at a location of the physical object. In one example, at this location of the physical object, the beam of light is focused ("focused beam of light"). For example, at this location the width of the beam of light is at its smallest value. Cross-sectional area of the light beam may have any shape. For example, the cross-sectional area may have circular shape or elliptic shape. The intensity of the focused beam of light varies along its transverse axis, which is perpendicular to its propagation axis. This transverse beam axis may be a radial axis. The light beam intensity at the center of the light beam is at its peak value, i.e. the beam intensity is at its maximum, and decreases along its transverse axis, forming an intensity distribution. This distribution may be approximated by a Gaussian function, as shown in FIG. 6. The width of the beam of light ("beam width") is defined as a length of line that intersects the intensity distribution at two opposite points at which the intensity is $1/e^2$ times of its peak value. The light beam may comprise more than one peak. The peak with highest beam intensity is used to calculate the beam width. An example of the beam width is schematically shown in FIG. 6. A typical beam width of a typical OCT system may vary in the range of 10 micrometers to 30 micrometers at the physical object location.

The OCT system may use a method that may further comprise acquiring data to form at least one B-scan cluster set. A number of at least one B-scan cluster set, P is equal to or larger than 1, wherein P is an integer. For example, P may be 1, 2, 3, 4, 5, 10, 100, 1,000, 10,000, or 100,000.

Each B-scan cluster set may comprise any number of B-scan clusters, N equal to or greater than 2, wherein N is an integer. For example, N may be 2, 3, 4, 5, 10, 100, 1,000, 10,000, or 100,000.

Each B-scan cluster may comprise any number of B-scans, M equal to or greater than 2, wherein M is an integer. For example, M may be 2, 3, 4, 5, 10, 20, 100, 1,000, 10,000, or 100,000.

Each B-scan may be located along the same transverse axis or another transverse axis (the x-axis or the y-axis) that may be parallel to those of other B-scans within the B-scan cluster set. Each B-scan may form a plane perpendicular to one of the transverse axes, and each B-scan plane may thereby be parallel to that of the other B-scans. That is, each B-scan may be parallel to the z-axis.

Each B-scan comprises plurality of data points, for example, located on the (x-z) plane. Each B-scan, each B-scan cluster, and each B-scan cluster set are acquired over a period of time. That is, each B-scan, each B-scan cluster, and each B-scan cluster set are formed at a different time than all other B-scans, B-scan clusters, and B-scan cluster sets, respectively. In this disclosure, "first formed" means first formed in time; "second formed" means second formed in time; "next formed" or "proximate" means next formed in time; and "last formed" means last formed in time.

The OCT motion contrast may be calculated for each (x,z) data point acquired over a period of time. This motion contrast may be calculated from a complex OCT signal, OCT intensity information, phase information, or a combination thereof.

Spatial distance between each B-scan plane within each B-scan cluster ("intra-cluster distance") may vary in the range of 0 to a half of the beam width in micrometers. For example, the intra-cluster distance may vary in the range of 0 to 15 micrometers.

Spatial distance between last formed B-scan of each B-scan cluster and first formed B-scan of another next B-scan cluster proximate to the said B-scan ("inter-cluster distance") may be at least equal to or greater than 1 micrometer. For example, the intra-cluster distance may vary in the range of 1 micrometer to 10 micrometers, 1 micrometer to 100 micrometers, or 1 micrometer to 1,000 micrometers.

Figure 7:
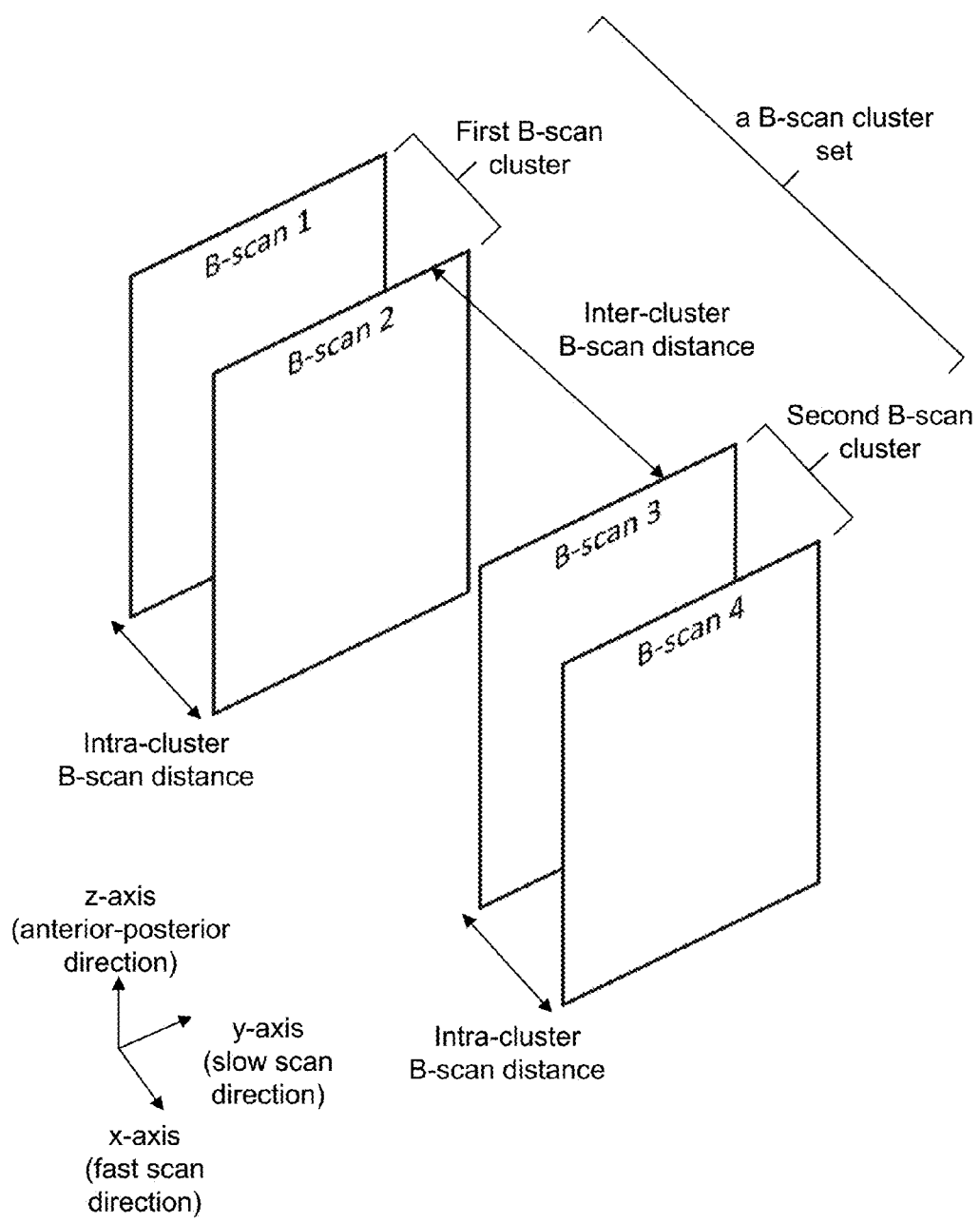
FIG. 7 schematically illustrates four B-scans, two B-scan clusters, and one B-scan cluster set by way of example that may be used for the calculation of an OCT phase sensitive B-scan registration

In an example, shown in FIG. 7, the first formed B-scan cluster comprises two B-scans and the second formed B-scan cluster comprises two B-scans. In this example, the B-scan cluster set comprises two B-scan clusters.

The method may further comprise acquiring data to form at least two B-scan cluster sets. Each B-scan cluster set may be located along the same transverse axis or another transverse axis (the x-axis or the y-axis) that may be parallel to those of other B-scan cluster sets. The spatial distance between last formed B-scan of each B-scan cluster set and first formed B-scan of another B-scan cluster set proximate to the said B-scan cluster set ("inter-cluster-set distance") may be at least equal to or greater than 20 micrometers.

While the sample motion during OCT image acquisition occurs in three dimensions, only the axial motion between two sequential B-scans may easily be identified. Transverse motion occurring during the acquisition of the two sequential B-scans may cause speckle noise in a measured OCT signal, which may not directly be identified. Also, although effects of the axial motion may be minimized by aligning and re-registering B-scans via OCT intensity-based alignment methods, such methods may introduce speckle and/or phase noise to OCT image contrast through the B-scans because the B-scans are not optimally aligned.

This disclosure relates to a method ("phase-sensitive B-scan registration") for minimization of effects of sample motion on the OCT image contrast. The phase-sensitive B-scan registration method may minimize effects of sample motion on the OCT image contrast in z-axis direction. This disclosure further relates to a method for minimization of effects of the sample motion between two sequential B-scans. The OCT signal may comprise an OCT signal intensity and/or phase.

The phase-sensitive B-scan registration method may comprise aligning the axial (z-axis direction) component of the motion to minimize the motion effects on the OCT signal ("axial alignment method"). Remaining phase noise may then directly be related to the transverse motion, which may have occurred.

This disclosure relates to an Optical Coherence Tomography (OCT) system that aligns all B-scans to correct for axial motion. The aligned all B-scans may be used to provide OCT image corrected for the axial motion.

A method for the axial alignment may comprise a phase-based axial alignment method between two sequential B-scans. This method may further comprise:
(a) Minimizing the phase noise introduced via the axial motion between the two B-scans, and/or
(b) Determining a quantitative metric that may be used to evaluate amount of transverse motion that may occur during the B-scans. This method may allow improved processing options and statistical outlier analysis for isolating data from the B-scans with largest motion noise.

The phase-sensitive B-scan registration method may comprise acquiring data to form at least two B-scans by using the OCT system. Two proximate B-scans may form a pair ("first formed B-scan and second formed B-scan" or "B-scan pair"). Each B-scan of the B-scan pair may comprise a number of A-scans, Q, where Q is an integer equal to or greater than 1. For example, Q may be 1, 10, 100, 1,000, or 10,000. Both B-scans of the B-scan pair may have same number of A-scans.

The phase-sensitive B-scan registration method may further comprise calculating at least three phase differences between the first formed B-scan and the second formed B-scan by shifting one of the B-scan pair relative to the other B-scan by a predetermined distance along the z-axis direction, using these phase differences to calculate a total phase error for each difference until finding a minimum value for the total phase error ("total phase error minimum"). The predetermined distance may be one pixel. That is, the shift may be (about) one pixel.

For example, the OCT system may have a configuration that scans a physical object that has a surface and a depth with a beam of light that has a beam width and a direction; acquires OCT signals from the scan; forms pixels from acquired OCT signals; forms at least one A-scan using the acquired OCT signals; forms at least one B-scan cluster set using the acquired OCT signals that includes at least one B-scan cluster that includes at least two B-scans that are parallel to one another and form planes that are parallel to the direction of the beam of light; and forms B-scan pairs from the at least two B-scans.

The OCT system may further have a configuration that (a) calculates a total phase error for each B-scan pair and shifts one B-scan of each B-scan pair in the direction of the beam of light at least two times, or (b) shifts one B-scan of each B-scan pair in the direction of the beam of light at least three times; wherein each shift is one pixel and parallel to the beam of light.

The OCT system may further have a configuration that calculates a total phase error for each B-scan pair after each shift; determines a minimum total phase error for each B-scan pair; determines an optimal shift for each B-scan pair; calculates the total distance that each B-scan has shifted at the end of the at shifts; and aligns all B-scans within the at least one B-scan cluster.

In this disclosure, "phase difference minimum" is "smallest calculated total phase error"; optimal shift is amount of shift identified at the phase difference minimum.

Figure 8:
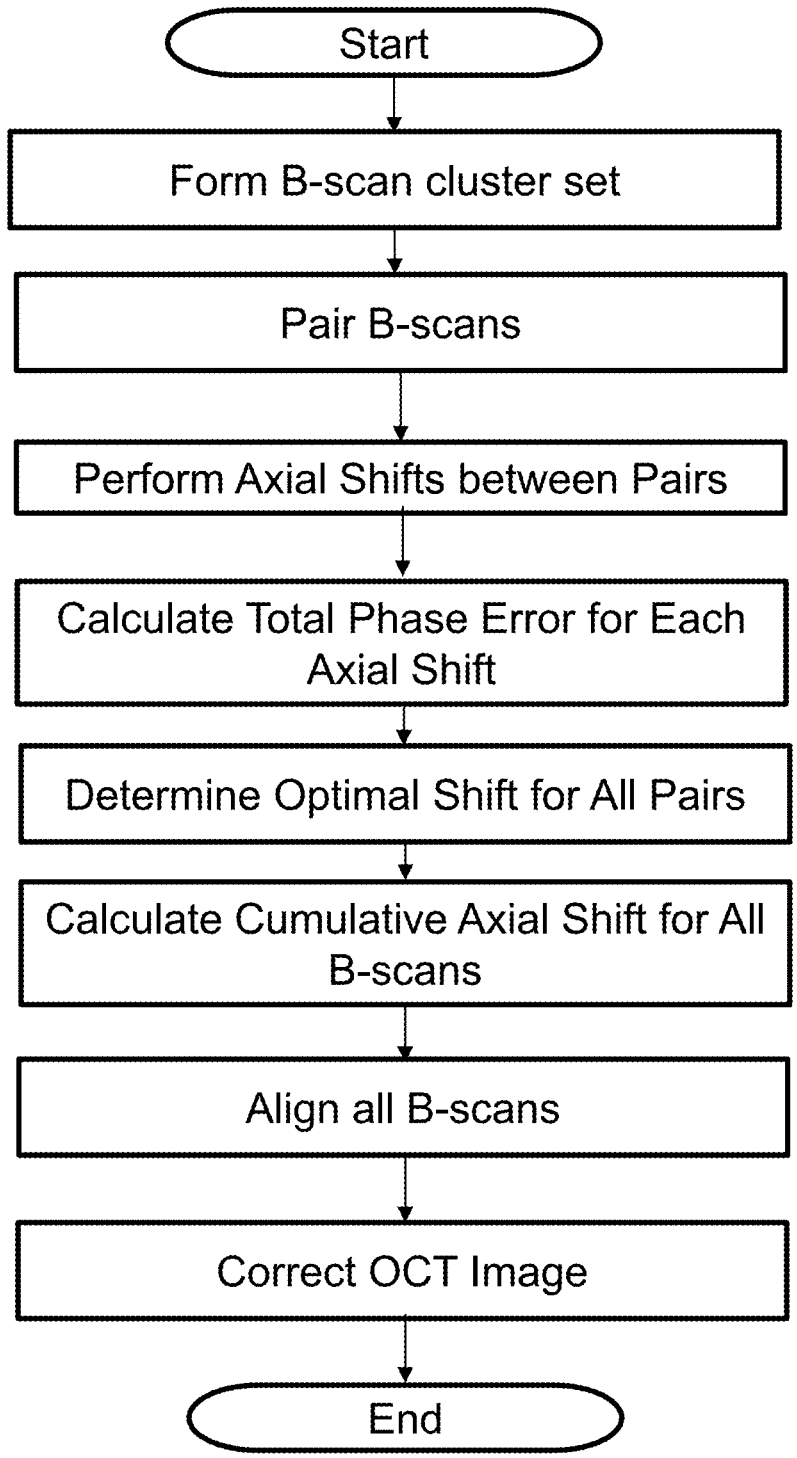
FIG. 8 shows how an OCT image may be corrected by using a phase-sensitive B-scan registration method.

An example of how this system may be used to correct an OCT image is schematically shown in FIG. 8 in a simplified manner.

Example 1. Calculating the Total Phase Error by Using the Calculated Phase Differences The total phase error may be calculated by using any method. The total phase error may be calculated by using the calculated phase differences. For example, the total phase error may be calculated by using the following equations.

$$\Delta\emptyset_{1,2}(x,z,\Delta z)=\mathrm{mod}(\emptyset_1(x,z)-\emptyset_2(x,z+\Delta z),2\pi) \qquad \text{Equation 1}$$

Where in Equation 1, $\emptyset_1(x,z)$ is the phase of a data point at $(x,z)$ location belonging to the first formed B-scan, $\emptyset_2(x,z+\Delta z)$ is the phase of a data point at $(x,z+\Delta z)$ location belonging to the second formed B-scan axially shifted by a distance of $\Delta z$, mod is the modulo of the phase difference between 0 and $2\pi$, and $\Delta\emptyset_{1,2}(x,z,\Delta z)$ is the phase difference between the phase of the data point of the first formed B-scan and the phase of the data point of the second formed B-scan.

The calculated $\Delta\emptyset_{1,2}(x,z,\Delta z)$ values for each data point provide a phase difference data point. These phase difference data points are used to calculate a bulk motion phase difference $\Delta\emptyset_{bulk}(x)$ by using any method available in the prior-art. For example, the bulk motion phase difference calculation method disclosed by Makita et al. "Optical coherence angiography" Opt. Express 14, 7821-7840 (2006) may be used. The content of this disclosure is incorporated herein in its entirety.

The phase difference may be corrected for the effects of the bulk motion by using the following equation:

$$\Delta\emptyset_{1,2\ corrected}(x=x_0,z,\Delta z)=\mathrm{mod}(\Delta\emptyset_{1,2}(x=x_0,z,\Delta z)-\Delta\emptyset_{bulk}(x=x_0),2\pi) \qquad \text{Equation 2}$$

Where in Equation 2, $\Delta\emptyset_{1,2\ corrected}(x=x_0,z,\Delta z)$ is the corrected phase difference, for each individual A-scan corresponding to a given x coordinate $x_0$.

Then, a thresholding method based on intensity is applied to the corrected phase difference by using any method available in the prior-art. For example, the thresholding methods disclosed by Fingler et al. This application is also based upon and claims priority to Patent Cooperation Treaty (PCT) application No. PCT/US15/14410, entitled "Optical Coherence Tomography (OCT) with Improved Motion Contrast," filed Feb. 4, 2015. The entire content of this disclosure is incorporated herein by reference.

Here $\Delta\emptyset_{1,2\ corrected,thresholding}(x,z,\Delta z)$ is the corrected phase difference with a thresholding method.

Finally, a total phase error may be calculated by using the following equation.

$$\text{Total Phase Error} = \Sigma_x \Sigma_y |\Delta\emptyset_{1,2\ corrected, thresholding}(x,z,\Delta z)|$$  Equation 3.

Figure 9:
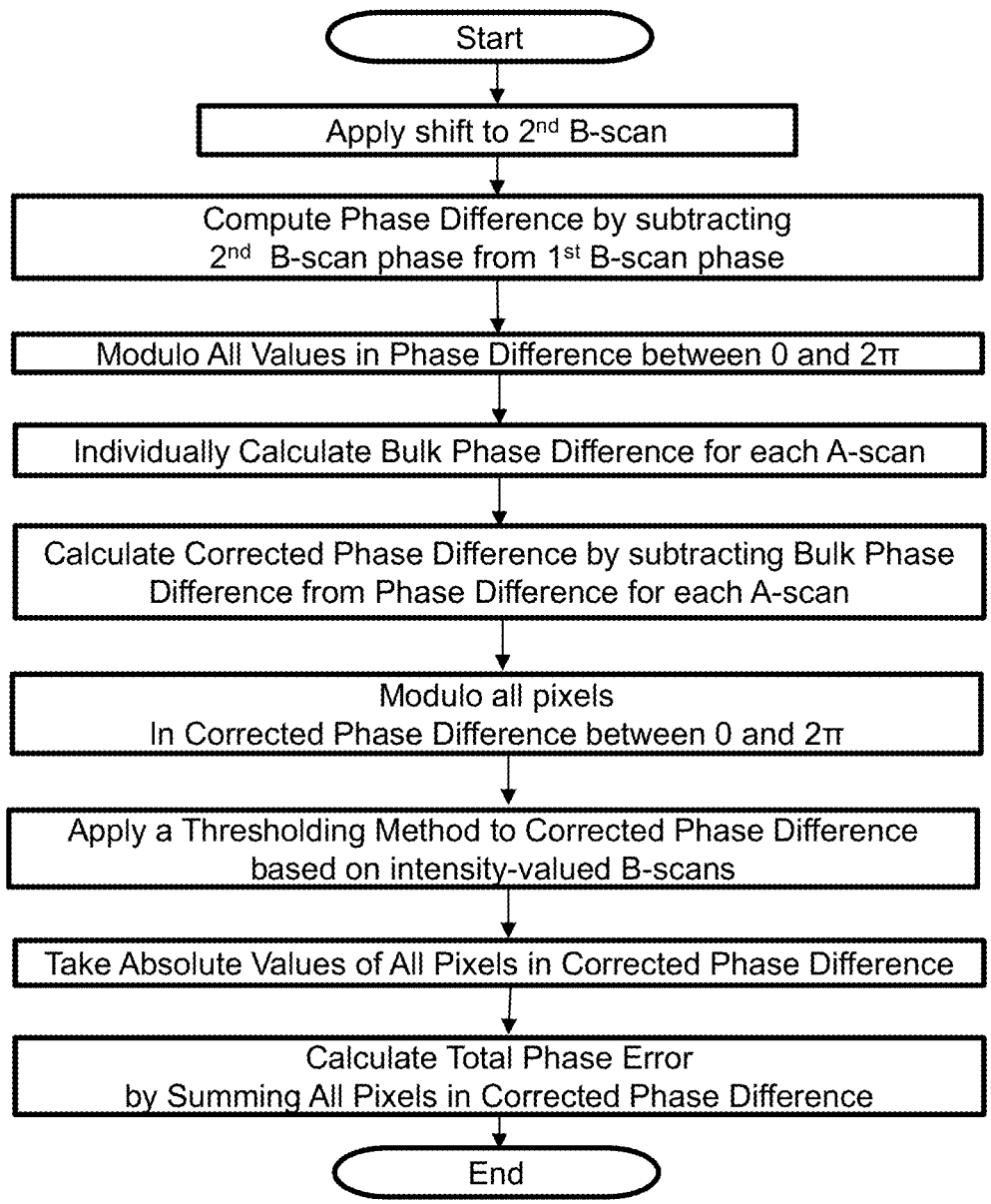
FIG. 9 schematically shows an exemplary method for how the total phase error may be calculated.

This method is schematically shown in FIG. 9.

Example 2. Finding the Total Phase Error Minimum

The phase difference may be found by any method. For example, first phase difference may be calculated by using the first formed B-scan and the second formed B-scan as acquired by the OCT system, without shifting the B-scan pairs relative to each other. That is, the first phase difference may be calculated for no shift.

Other phase differences may be calculated by first shifting the second formed B-scan, relative to the first formed B-scan, along the z-axis. The shift may be one pixel. For example, the calculating a phase difference may comprise choosing a number of shifts, T on one of the B-scan pairs (e.g. the first formed B-scan), where T is an integer equal to or greater than 3. For example, T may be 3 shifts, 4 shifts, 5 shifts, 10 shifts, or 100 shifts.

The shifting may be done in any direction along the z-axis. One such direction is hereafter referred as "positive direction" and the other direction opposite to the positive direction is hereafter referred as "negative direction". For example, the other phase differences may be calculated by first shifting the second formed B-scan, relative to the first formed B-scan, one pixel shift by one pixel shift along the z-axis in the positive direction and then calculating the phase difference between the B-scan pair for each shift.

Each of these calculated phase differences are used to calculate a total phase error for each shift. The total phase error for each shift may be calculated, for example, by using the methods disclosed in Example 1. If the total phase error decreases after each shift, the second B-scan may further be shifted along the positive direction one pixel by one pixel until the total phase error increases. A minimum of the total phase error is thereby found.

If the total phase error increases after one shift in the positive direction, the other total phase error may be calculated by shifting the second B-scan, relative to the first formed B-scan, one pixel by one pixel along the z-axis in the negative direction and then calculating the total phase error between the B-scan pair for each shift. If the total phase error decreases after each shift, the second B-scan may further be shifted along the negative direction one pixel by one pixel until the total phase error increases. A minimum of the total phase error is thereby found.

Figure 10:
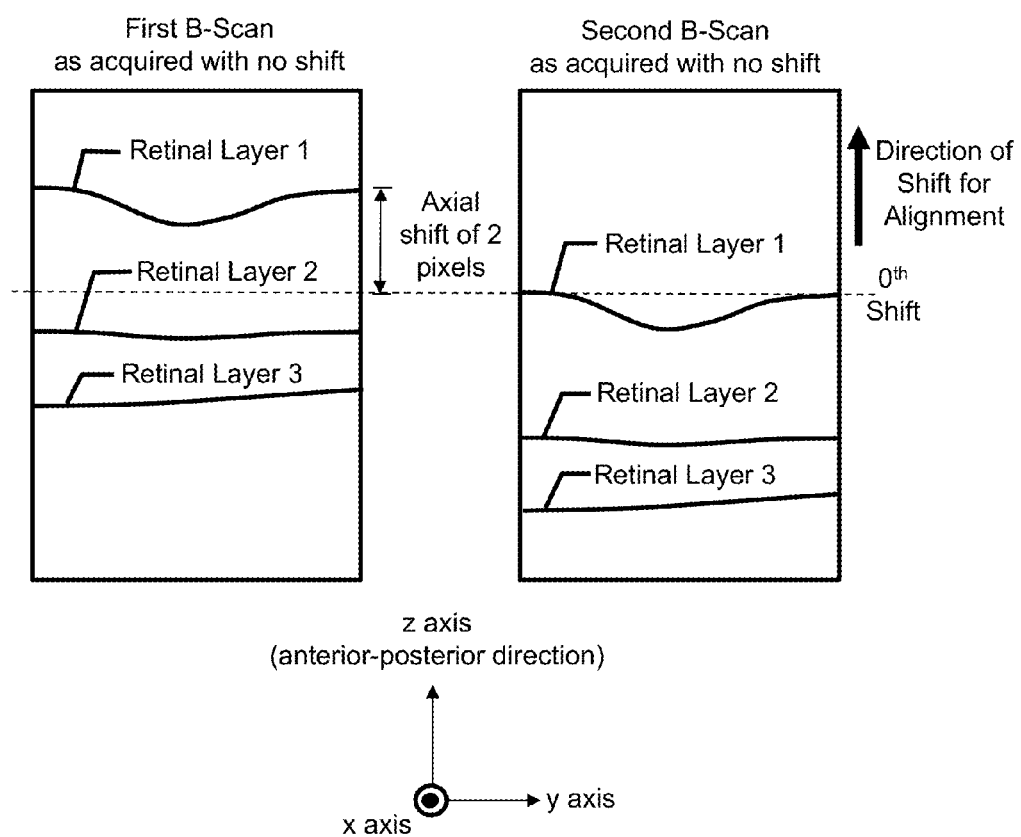
FIG. 10 shows an example of a shift of the second B-scan due to motion in z-axis direction.
Figure 11:
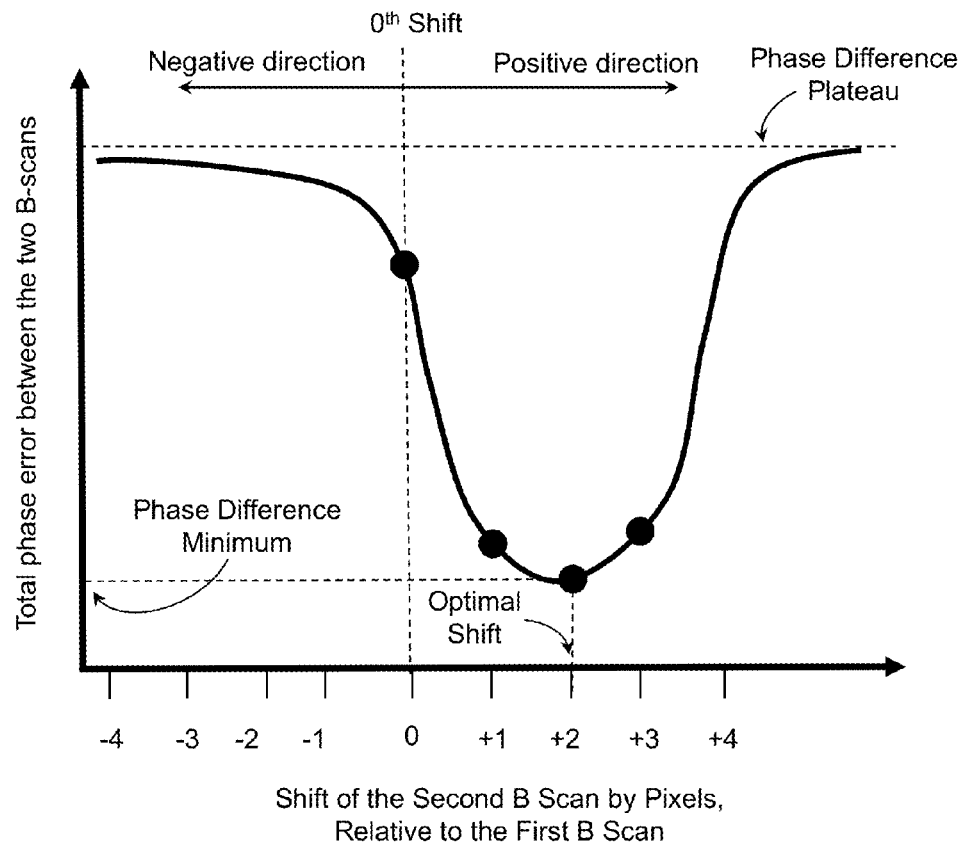
FIG. 11 shows an example of determination of a phase difference minimum and an optimal shift.

This method is schematically shown by way of example in FIGS. 10-11. In this demonstrative example, position of the three retinal layers (shown in a simplified manner) has shifted by 2 pixels in the negative direction (e.g. posterior direction) due to motion effects occurring when the first formed B-scan and the second formed B-scan are being acquired. See FIG. 10. To correct for this motion, the total phase error between the first formed B-scan and the second formed B-scan for no shift, 1 pixel shift, 2 pixel shift, 3 pixel shift and 4 pixel shift in the positive direction (e.g. anterior direction) are first calculated. Then, a location of the total phase error is thereby determined from these calculations as 2 pixels in the positive direction, as shown in FIG. 11. The shift amount for this example is 2 pixels.

Example 3. Calculating Cumulative Axial Shift for Each B-Scan within a B-Scan Cluster The cumulative axial shift for each B-scan within a B-scan cluster may be calculated by using any method. A reference B-scan may be chosen and other B-scans within the cluster may be aligned with this reference B-scan. This reference B-scan may be any B-scan within a B-scan cluster. For example, the reference B-scan may be the first formed B-scan belonging to the B-scan cluster. Following example is explained with respect to this first formed B-scan. However, any other B-scan may be chosen to achieve the same end result.

In this method, for example, each two B-scans proximate (i.e. adjacent) to each other may form a B-scan pair. The reference B-scan may be the first formed B-scan belonging to the B-scan cluster. A location of the minimum of the total phase error for each B-scan pair may be determined in the manner disclosed in Example 2. This is the optimal shift, $\Delta z_{optimal,j}$ between the B-scans forming the B-scan pair as defined by the following equation:

$$\Delta z_{optimal,j} = \text{Optimal Shift between } B\text{-scan } j-1 \text{ and } B\text{-scan } j$$  Equation 4.

Where $\Delta z_{optimal,j}$ is $\Delta z$ corresponding to the minimum total phase error.

The cumulative axial shift for each B-scan within the B-scan cluster may be determined by calculating $\Delta z_{optimal,j}$ for each B-scan pair and adding them by using following equations:

$$\Delta z_{cumulative,j} = \text{Cumulative Axial Shift for } B\text{-scan } j$$  Equation 5.

$$\Delta z_{cumulative,j} = \Sigma_{k=1}^{j} \Delta z_{optimal,k}$$  Equation 6.

Example 4

Two B-scans are compared for 7 relative axial positions. A boolean intensity threshold may be used, which is based on averaged intensity image for each of these alignment positions, choosing a threshold value just above the noise level of the individual OCT intensity images. For each of these axial realignment positions, e.g. for each z position, the two A-scans are compared through calculating the change in phase between them, and the bulk axial motion may be calculated for this A-scan pair and the phase changes are corrected and adjusted based on phase wrapping using the modulus of $2\pi$. Once this is calculated for each A-scan pair, the absolute values of the thresholded, corrected phase changes may be summed across the entire B-scan. These summations may be calculated for each axial change orientation, and normalized to the highest value of this group, producing the normalized phase summation. The axial alignment that may result in the minimum value of the normalized phase summation may be the optimal axial alignment to minimize the phase noise, and the minimum phase summation value at that alignment may be associated with the transverse motion that has occurred during the acquisition.

Example 5

If the axial re-alignment is significant, it may be possible that the optimum axial alignment for one portion of the B-scan may not be the same as the other portions. This processing algorithm can be used on fractions of the entire B-scan separately, to validate the same registration for all fractions in general, and identify the cases which need additional processing and attention to address this variability in sample axial motion.

Example 6

In this example, processing speed is improved. In above axial realignment methodology, the B-scan to B-scan phase change calculations are performed for R axial orientations. Rather than calculating all of these orientations by default, speed improvements may be achieved by only initially calculating fewer cases, such as for axial change $\Delta z=R, 0, 1$ and $-1$, where R is an integer. In general, $\Delta z=1, 0, -1$ may give enough data to identify cases where optimum axial re-alignment is 0, and in other cases may identify which additional calculations need to be pursued to achieve the optimal alignment. If the minimum metric of the set is at $\Delta z=1$, then $\Delta z=2$ may be calculated to identify which may actually be the minimum or whether additional calculations may be required. The case at $\Delta z=R$ should provide enough decorrelation to normalize the metric being used to evaluate the transverse motion noise.

Example 7

Instead of performing the axial re-alignment and phase correction on every A-scan within the two B-scans, a selection of A-scans may be chosen, as a representative set spread out across the entire B-scan. For this variation, optimal axial realignment may be achieved in multiple ways, including but not limited to: (a) Either comparing A-scan to A-scan axial realignment individually, or (b) Re-aligning all A-scans within this chosen selection together to identify the optimal axial alignment, and thereby reducing errors induced by phase error-inducing features such as major vasculature that would affect some of the individual A-scan comparisons.

The OCT method disclosed above may be used for any OCT related application. For example, this method maybe used in forming larger field of view OCT images of the physical object. This method may be incorporated into methods and systems related to OCT based angiography. For example, the choroidal vasculature may be identified in more detail by using the OCT motion contrast method. The OCT methods comprising the OCT motion contrast method also be used in diagnosis and/or treatment of health conditions such as diseases. For example, the OCT methods comprising the OCT motion contrast method may be used in characterization of retinal health.

The OCT system disclosed above may provide any information related to the physical object. For example, this system, which may use the motion contrast method, may provide 2D (i.e. cross-sectional) images, en-face images, 3-D images, metrics related to a health condition, and the like. This system may be used with any other system. For example, the OCT system may be used with an ultrasound device, or a surgical system for diagnostic or treatment purposes. The OCT system may be used to analyze any physical object. For example, the OCT system may be used in analysis, e.g. formation of images, of, for example, any type of life forms and inanimate objects. Examples of life forms may be animals, plants, cells or the like.

Unless otherwise indicated, the processing unit 140 that has been discussed herein may be implemented with a computer system configured to perform the functions that have been described herein for this unit. The computer system includes one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The computer system for the processing unit 140 may include one or more computers at the same or different locations. When at different locations, the computers may be configured to communicate with one another through a wired and/or wireless network communication system.

The computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

Any combination of methods, devices, systems, and features disclosed above are within the scope of this disclosure.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. An optical coherence tomography (OCT) system having a configuration that:
   scans a physical object that has a surface and a depth with a beam of light that has a beam width and a direction;
   acquires OCT signals from the scan;
   generates discretized A-scan data and B-scan data from the acquired OCT signals;
   assigns the discretized A-scan data into pixels;
   forms at least one B-scan cluster set using the acquired OCT signals that each includes at least one B-scan cluster that includes at least two B-scans that are parallel to one another and form planes that are parallel to the direction of the beam of light;
   forms B-scan pairs from the at least two B-scans in each B-scan cluster;
   does either of the following:
      calculates a total phase error for each B-scan pair before any shift of any B-scan and then shifts one B-scan of each B-scan pair at least two times, or
      shifts one B-scan of each B-scan pair at least three times;
   wherein each shift is one pixel and in a direction parallel to the beam of light;
   calculates a total phase error for each B-scan pair after each shift;
   identifies the smallest calculated total phase error among all of the calculated total phase errors for each B-scan pair;
   identifies the shift amount for each B-scan pair that resulted in the identified smallest calculated total phase error;
   calculates a cumulative axial shift for each B-scan within the at least one B-scan cluster; and
   aligns all B-scans within the at least one B-scan cluster.

2. The OCT system of claim 1, wherein:
   the OCT system has a configuration that, after forming the B-scan pairs, calculates phase differences for each B-scan pair;
   each total phase error is calculated using the calculated phase differences; and
   each calculated phase difference constitutes a phase difference data point.

3. The OCT system of claim 2, wherein the phase difference data points are used to calculate a bulk motion phase difference.

4. The OCT system of claim 3, wherein the calculated bulk motion phase difference is corrected for effects of bulk motion to provide a corrected phase difference.

5. The OCT system of claim 4, wherein a threshold ing method based on intensity is applied to the corrected phase difference.

6. The OCT system of claim 1, wherein the OCT system has a configuration that forms the B-scan pairs that includes A-scan pairs from and uses all or a fraction of the A-scan pairs within the B-scan pairs to calculate a total phase error for each B-scan pair; wherein one A-scan of the A-scan pair is within one of the B-scans of the B-scan pairs and the other A-scan of the A-scan pair is within the other B-scan of the B-scan pair.

7. The OCT system of claim 1, wherein the OCT system has a configuration that uses the aligned B-scans to form an image of the physical object.

8. The OCT system of claim 1, wherein the physical object is human tissue.

9. The OCT system of claim 1, wherein the OCT system comprises:
   at least one light source that provides the beam of light;
   at least one retro-reflector;
   at least one optical fiber coupler or at least one free space coupler that guides the beam of light to the physical object and to the at least one retro-reflector; wherein the beam of light guided to the physical object forms at least one backscattered light beam; and wherein the at beam of light guided to the at least one retro-reflector forms at least one reflected reference light beam;
   at least one scanning optic that scans the at least one light beam over the physical object;
   at least one detector that:
      combines the at least one backscattered light beam and the at least one reflected light beam to form light interference,
      detects magnitude and time delay of the at least one backscattered light beam, and
      forms OCT signals;
   wherein the at least one optical fiber coupler or the at least one free space coupler guides the at least one backscattered light beam and the at least one reflected light beam to the at least one detector;
   at least one processor that obtains and analyzes the OCT signals formed by the at least one detector, and forms at least one image of the physical object; and
   at least one display that displays the at least one image of the physical subject.

10. The OCT system of claim 9, wherein the OCT system has a configuration that identifies regions of motion based on intensity or phase variations between the B-scans.

11. The OCT system of claim 10, wherein the OCT system has a configuration that identifies the regions of motion using a Phase Variance OCT (PV-OCT) method, a Phase Contrast OCT (PC-OCT) method, an Intensity/Speckle Variance OCT (IV-OCT) method, a Doppler OCT (D-OCT) method, a Power of Doppler Shift OCT (PDS-OCT) method, a Split Spectrum Amplitude Decorrelation Analysis (SSADA) method, an Optical Micro-angiography (OMAG) method, a Correlation Mapping OCT (cmOCT) method, or a combination thereof.

12. The OCT system of claim 10, wherein the OCT system has a configuration that uses a Phase Variance OCT (PV-OCT) method.

13. Non-transitory, tangible, computer-readable storage media containing a program of instructions that causes a computer system running the program of instructions to function as an optical coherence tomography (OCT) system, including to:
- scan a physical object that has a surface and a depth with a beam of light that has a beam width and a direction;
- acquire OCT signals from the scan;
- generate discretized A-scan data and B-scan data from the acquired OCT signal;
- assign the discretized A-scan data into pixels;
- form at least one B-scan cluster set using the acquired OCT signals that each includes at least one B-scan cluster that includes at least two B-scans that are parallel to one another and form planes that are parallel to the direction of the beam of light;
- form B-scan pairs from the at least two B-scans in each B-scan cluster;
- do either of the following:
  - calculate a total phase error for each B-scan pair before any shift of any B-scan and then shifts one B-scan of each B-scan pair at least two times, or
  - shifts one B-scan of each B-scan pair at least three times;
- wherein each shift is one pixel and in a direction parallel to the beam of light;
- calculate a total phase error for each B-scan pair after each shift;
- identify the smallest calculated total phase error among all of the calculated total phase errors for each B-scan pair;
- identify the shift amount for each B-scan pair that resulted in the identified smallest calculated total phase error;
- calculate a cumulative axial shift for each B-scan within the at least one B-scan cluster; and
- align all B-scans within the at least one B-scan cluster.

14. The storage media of claim 13 wherein the program of instructions causes the computer system running the program of instructions to:
- obtain and analyze the OCT signals formed by at least one detector, and form at least one image of the physical object; and
- display the at least one image of the physical subject.

* * * * *